Sept. 26, 1933. R. SHIBUYA Plant Pat. 75

SINGLE CHRYSANTHEMUM

Filed Nov. 10, 1931

INVENTOR.
Ryohitsu Shibuya.

BY

Townsend & Loftus.
ATTORNEYS.

Patented Sept. 26, 1933

Plant Pat. 75

UNITED STATES PATENT OFFICE

75

SINGLE CHRYSANTHEMUM

Ryohitsu Shibuya, Menlo Park, Calif.

Application November 10, 1931
Serial No. 574,061

1 Claim. (Cl. 47—60)

This invention relates to improvements in chrysanthemums of the type known as single chrysanthemums.

In the growing of chrysanthemums the color of the flower and the blooming period are important factors, this being particularly true when chrysanthemums are grown by nursery-men for cutting and sale to wholesale florists and the like. In California chrysanthemums of the type referred to usually commence blooming in the early part of October and, as large quantities are grown, the market is quickly flooded, hence if a chrysanthemum is developed which will bloom earlier and which at the same time has color appeal, the importance thereof can readily be appreciated.

By pollinization of chrysanthemums through several generations, I have developed a single chrysanthemum which blooms approximately one month earlier than any other type of single chrysanthemum which has come to my attention, and which at the same time carries flowers of a distinctly new color, to-wit, a bronze color.

The new strain or type developed by me is shown in the accompanying drawing, in which—

Figure 1:
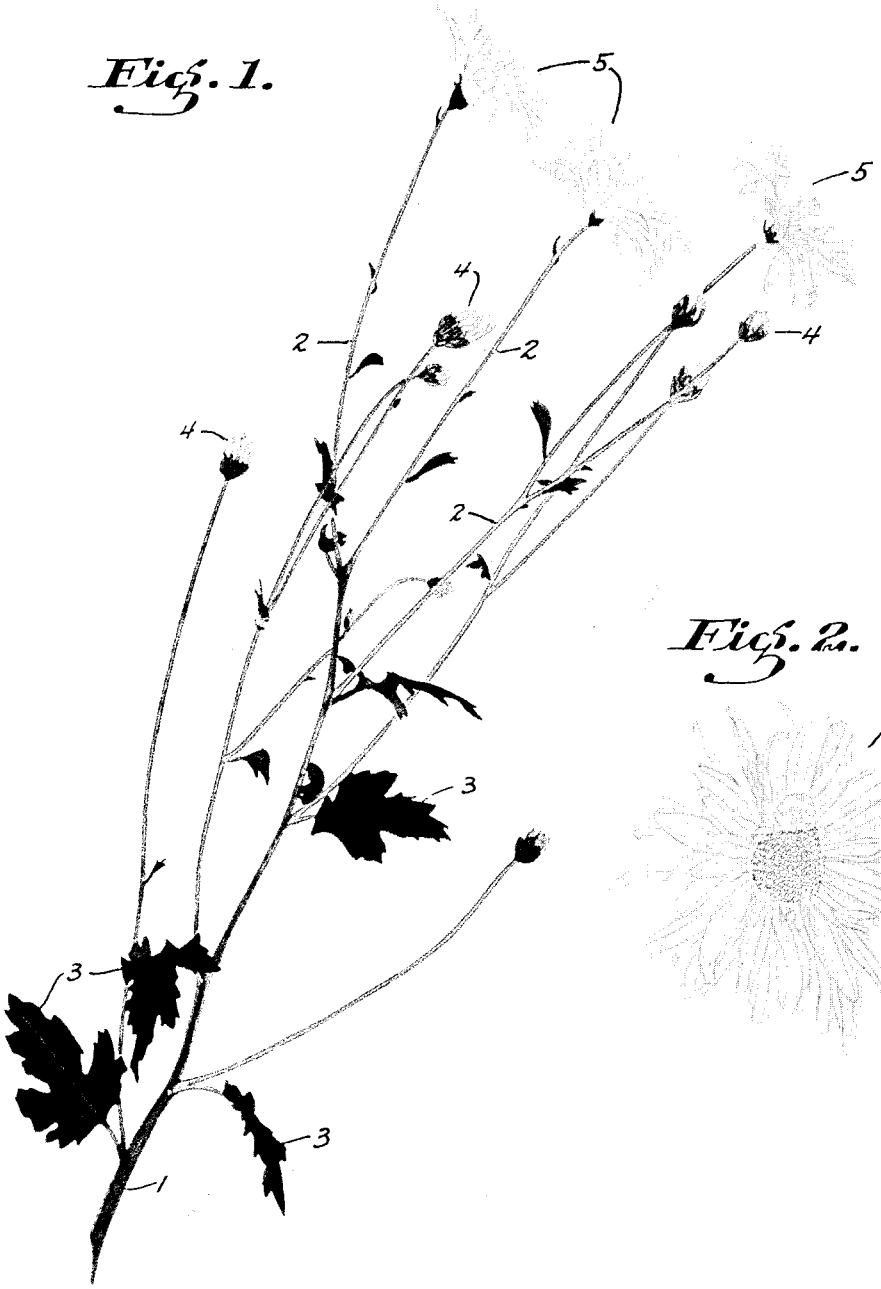
Figure 2:
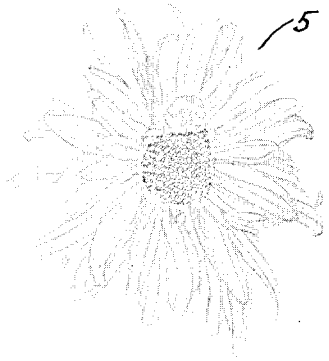

Fig. 1 is a perspective view painted in water colors, showing the color of the flowers, buds, stems, leaves, etc., and Fig. 2 is a face view showing the average size of the flower as grown.

In the drawing, 1 indicates the main stem of the chrysanthemum, 2 side stems or shoots, 3 the leaves, 4 the terminal buds, and 5 the flowers.

I have developed this new variety of chrysanthemum by cross-pollinization of a variety known as the "Bronze Buckingham" and a variety known as "Shibuya Seedling 1926 O. G.". The variety produced by this cross and described here flowers approximately one month earlier than the "Bronze Buckingham". Its petals are narrower and have more pointed tips and its color just a little lighter shade than the "Bronze Buckingham". It is also characterized by slender and smaller plants and has leaves of slightly brighter color and more deeply serrated than average. It is definitely not a sport, but a cross of seedling plants of the two above named varieties.

The average size of the flower developed is that shown in Fig. 2. The flowers have the color shown, to-wit, a bronze color. Besides developing a new color strain, I have also developed a chrysanthemum which commences blooming in the early part of September, approximately one month earlier than chrysanthemums of the same type of which there are several.

The plant is asexually reproduced either by root division or slipping. The type of chrysanthemum developed is a profuse bloomer.

Having thus described my new type of single chrysanthemum, what I claim is—

A single chrysanthemum plant as herein shown and described characterized by being an early bloomer, by carrying blooms of a light bronze color, but having a small bloom with narrow pointed tipped petals, slender stems on a small plant, and comparatively bright deeply serrated leaves.

RYOHITSU SHIBUYA.